United States Patent [19]

Finkenaur et al.

[11] Patent Number: 4,935,228

[45] Date of Patent: Jun. 19, 1990

[54] LIP GLOSS

[75] Inventors: Geoffrey D. Finkenaur, Clintondale; Robert A. Weber, Suffern, both of N.Y.

[73] Assignee: L'Oreal S.A., Paris, France

[21] Appl. No.: 138,326

[22] Filed: Dec. 28, 1987

[51] Int. Cl.$^5$ .......................... A61K 7/25; A61K 7/27
[52] U.S. Cl. ........................................ 424/64; 424/53; 514/944; 252/315.1
[58] Field of Search ..................... 424/64, 83; 514/944; 252/315.1; 585/12, 13

[56] References Cited

U.S. PATENT DOCUMENTS

| | | | |
|---|---|---|---|
| 3,215,599 | 11/1965 | Thau et al. | 424/83 |
| 3,642,635 | 2/1972 | Macleod | 424/83 X |
| 3,764,537 | 10/1973 | Macleod | 424/83 X |
| 3,876,761 | 4/1975 | Shepard | 424/81 X |
| 4,164,564 | 8/1979 | Chen | 424/83 |
| 4,438,140 | 3/1984 | Guillon et al. | 424/64 X |

OTHER PUBLICATIONS

"Modern Ointment Base Technology I, Properties of Hydrocarbon Gels" by Margaret N. Mutimer et al. published in the Journal of the American Pharmaceutical Association in Feb. of 1956, vol. XLV, No. 2, pp. 101–105.

"A New Procedure for the Preparation of Polyethylene–Mineral Oil Gels," by Paul Thau and Charles Fox, J. Soc. Cosmetic Chemists 16, 359–363, (1965).

Primary Examiner—Thurman K. Page
Assistant Examiner—Susan S. Rucker
Attorney, Agent, or Firm—Brumbaugh, Graves, Donohue & Raymond

[57] ABSTRACT

A lip gloss comprising a mineral oil gel comprising polyethylene and an ethylene-vinyl acetate copolymer, wherein the weight proportion of polyethylene to ethylene-vinyl acetate copolymer is in the range of 90:10 to 70:30, respectively where polyethylene is present in major proportion, and wherein the weight proportion of polyethylene to ethylene-vinyl acetate copolymer is in the range of 20:80 to 30:70, respectively, where the ethylene-vinyl acetate is present in major proportion; a preferred embodiment includes 43% or less by weight of a wear-enhancing agent selected from the group consisting of polyiso and normal butene, lanolin and dimethylpolysiloxane.

5 Claims, No Drawings

LIP GLOSS

FIELD OF THE INVENTION

This invention relates to cosmetic compositions. More particularly, the invention relates to lip gloss compositions in the form of stable thermoplastic gels having constant rheological properties in the temperature range of from about 4° C. to 45° C.

BACKGROUND OF THE INVENTION

The art of preparing polyethylene-mineral oil gels for use in dermatological preparations and cosmetic formulations is well developed. The article "Modern Ointment Base Technology I, Properties of Hydrocarbon Gels" by Margaret N. Mutimer et al. published in the *Journal of the American Pharmaceutical Association* in February of 1956, Volume XLV, No. 2, Pages 101-105, describes the state of the art at that time. Another article, "A New Procedure for the Preparation of Polyethylene—Mineral Oil Gels", by Paul Thau and Charles Fox, *J. Soc. Cosmetic Chemists* 16, 359-363 (1965), describes a procedure for making gels of this type, utilizing high shear mixing equipment to maintain a firm dispersion of the ingredients during the critical phase of the cooling process. U.S. Pat. No. 3,215,599 describes a related process for making an unctuous product.

SUMMARY OF THE INVENTION

It has now been found that a lip gloss of highly desirable characteristics is provided by a mineral oil gel system containing both polyethylene and an ethylene-vinyl acetate copolymer, the gel being thermoplastic and one which maintains a desirable and substantially constant consistency over the temperature range of 4° C. to 45° C. Furthermore, in order to obtain the desired results of this invention, the polyethylene and the ethylene-vinyl acetate copolymer must be present in certain critical ranges of proportions. In compositions having more polyethylene than ethylene vinyl acetate copolymer, the two materials must be present in the range of proportions by weight, respectively, of 90:10 to 70:30, with 75:25 being preferred. On the other hand, in compositions having less polyethylene than ethylene-vinyl acetate copolymer, the two materials must be present in the range of proportions, by weight, respectively, of 20:80 to 30:70, with 25:75 being preferred.

It has further been found that a preferred embodiment is realized when the lip gloss additionally contains a wear-enhancing agent selected from the group consisting of poly iso and normal butene, lanolin, and dimethylpolysiloxane. The most preferred embodiment incorporates a poly iso and normal butene as the wear-enhancing agent.

DETAILED DESCRIPTION OF THE INVENTION

The lip gloss compositions of the present invention are compositions used for cosmetic and lip care purposes and specifically for lip coloring, in much the same manner as lipstick is used. These products are generally low pigmented, high shine lip preparations. The lip gloss can be applied to the lips directly from applicators by simple extrusion in a manner similar to preparations now employed to treat chapped lips. Accordingly, they have a flowable, extrudable consistency and are readily moved about the surface of the lips in a desired pattern simply by using the applicator tip.

In order to function satisfactorily as a lip gloss, the compositions of the present invention must possess certain required flow characteristics. The composition must have sufficient viscosity to prevent its leakage from the container and must be able to retain the color and other ingredients of the system in uniform suspension or dispersion. It must be readily spreadable on lips and must be retained on the lips for a reasonable length of time. It is also important that the viscosity and other characteristics initially achieved in the system be retained over the entire period of storage of the lip gloss so that its performance is the same after six months of storage on a store shelf as it is when initially prepared. A further requirement is that the lip gloss retain a desired consistency and viscosity over the temperature range of expected use; in practice, this means a temperature range of about 4° C. to 45° C.

In accordance with the present invention, an extremely stable lip gloss system is provided by a polyethylene-mineral oil gel system in combination with an ethylene-vinyl acetate copolymer. The presence of the copolymer in the proper proportions retards viscosity development and maintains the resulting gel at a constant stability over a broad range of temperatures and over a long period of storage.

The viscosity range required for the lip gloss of this invention will range in accordance with the type and design of the container from which it is dispensed. One suitable package is a co-extruded low density polyethylene tube with stiff shoulder wall construction and an applicator having a 0.1 mm orifice. A lip gloss composition for use in a container having these specifications may have a viscosity within the range of 95,000 to 300,000 c.p.s., as determined on a Brookfield Helipath RVT Viscometer using a T-F Spindle at 10 rpm and at 25° C. The optimum range of viscosity is 200,000 to 300,000 c.p.s. For packages of the same volume and with a smaller applicator orifice and softer side walls, a lip gloss composition having a minimum viscosity of about 45,000 c.p.s. determined on the same basis, can be used.

Broadly speaking the polyethylene-mineral oil gel systems used in accordance with the present invention may be any of those known to the art, including those discussed in the Mutimer et al. reference and the Thau et al. reference discussed above. The ethylene-vinyl acetate copolymer is incorporated into the gel system at the same time and in the same manner as the polyethylene.

In preparing the polyethylene-mineral gel systems usable in the present invention, it is noted that polyethylenes having molecular weights between 1,000 and 25,000 may be used. Polyethylenes with molecular weights below this level provide weak, unstable gels, while those of higher molecular weight, require too long a time to dissolve, with a resulting excessive heating of the mineral oil constituent.

The ethylene copolymer with vinyl acetate which may be used in accordance with this invention, may have a molecular weight within the range of 2000-3000, and is preferably one having a molecular weight of 2,000-2,500. This material is added to the mixture of polyethylene and mineral oil during initial stages of the gel system preparation, i.e. it is added before the ingredients are heated and thus is present during the critical phase of the cooling process.

Optimum results are obtained when the polyethylene and the ethylene-vinyl acetate are present in the compositions in a proportion, by weight, of 25% of one and 75% of the other. In other words, lip gloss compositions of this invention containing polyethylene and ethylene-vinyl acetate in the weight proportions, respectively, of 25:75 and 75:25 each provide optimum results. In compositions where polyethylene is the minor component of the combination, the two polymers should be present in a range of proportions, respectively, of 20:80 to 30:70. On the other hand, when polyethylene predominates in the mixture, it must be present in a range of proportions, by weight, of 90:10 to 70:30. Surprisingly, it has been found that compositions containing equal parts of polyethylene and ethylene-vinyl acetate copolymer provides unacceptable results.

In accordance with another preferred embodiment of the present invention, a wear-enhancing agent such as a poly iso and normal butene, lanolin, or dimethyl polysiloxane is added. This material makes the lip gloss more waterproof and permits it to retain its coloring and other beneficial effect on the wearer's lips for a substantially longer period. Without the agent, the lip gloss disappears within about 30 minutes.

The level of wear-enhancing agent used may vary, depending on the extent of improvement desired. Where the wear-enhancing agent is poly iso and normal butene at a level of about 43% of the total composition, lip gloss has been found to last as long as three hours on the lips of the wearer. Lesser amounts provide reduced wear. Amounts substantially in excess of this amount have adverse affects on the stability of the gel.

Coloring agents normally used in lipstick formulations are useful in the compositions of this invention, and at the same levels. Examples of suitable agents include FDA approved organic and inorganic pigments such as titanium dioxide, D and C. red #6 barium lake, synthetic iron oxide and the like. These materials may be incorporated at levels ranging from 1 to 8% by weight.

Other conventional lipstick ingredients such as Paraban antimicrobials, antioxidants, vitamins, anti-inflammatory agents such as sodium hylorinate, and sun screens such as esters of 4- (Dimethylamino)benzoic Acid and oxybenzone may be used.

The lip gloss formulations of the present invention are prepared by first charging the ingredients into a jacketed stainless steel kettle with a counter-agitating sweep mixer. The mixture is heated to the recommended melting temperature of the polyethylene by introducing steam into the jacket and agitation is commenced. When the mixture is completely melted and homogeneous, it is allowed to cool to a temperature of about 5° C. above the cloud point of the mixture of polymers in the mineral oil. Rapid cooling is then commenced by introducing cold cooling water into the jacket until a temperature of 10° C. below the cloud point of the mixture is achieved while maintaining agitation. This step may be accomplished by providing 10° C. cooling water to the jacket of the kettle and by agitation until the desired temperature is reached. After the rapid cooling step, the composition is further cooled with agitation until the desired viscosity is obtained. The batch is then charged into an appropriate holding vessel and used to fill retail containers of the lip gloss.

The rapid cooling step of the above-described process is preferably carried out at the rate of 1.5° C. per minute. It is also noted that the initial temperature to which the mixture is heated is that of the highest melting point of the polymer ingredients. The following table gives the melting point and cloud points of several suitable polyethylenes and ethylene-vinyl acetate copolymers:

|   |   | Melting Pt. (in °C.) | Cloud Pt. in Mineral Oil (in °C.) |
|---|---|---|---|
| Homopolymer Polyethylenes | | | |
| (1) | A-C 9 (Allied Chemical Corporation) | 117 | 90 |
| (2) | A-C 617 (Allied Chemical Corporation) | 102 | 79 |
| (3) | Epolene N-34 (Eastman Chemicals) | 117 | NA |
| (4) | Epolene Wax-12 (Eastman Chemicals) | 117 | NA |
| Ethylene-Vinyl Acetate Copolymers | | | |
| (1) | A-C 400 (Allied Chemical Corporation) | 95 | NA |
| (2) | A-C 430 (Allied Chemical Corporation) | 60 | NA |

The wear-enhancing agents used in accordance with the present invention include poly iso and normal butene, lanoline, and dimethylpolysiloxane. The polyiso and normal butene may be those supplied by the AMACO Chemical Corporation under the trademark INDOPOL. Grades denominated H-100, H-300, H-1500, and H-1900 have been investigated. The preferred compound is the H-1500. The H-1900 provides a product which is excessively viscous. H-100 and H-300 provide acceptable results.

Various silicones have also been investigated. Dow Corning 200 Fluid, a dimethyl polysiloxane, both grade 100,000 CS viscosity and grade 600,000 CS viscosity performed satisfactorily as wear-enhancers.

Anhydrous lanolin also functioned satisfactorily as a wear-enhancing agent.

These materials are used at a level of 20 to 50%, by weight, preferably at levels of 35-45% by weight of the total composition, individually, or in combination.

The invention will be further described by reference to the following examples:

EXAMPLE 1

The following general procedure was used in preparing the compositions illustrated in Examples 2, 3, 4 and 5.

All ingredients were charged into a stainless steel kettle having a steam/cooling jacket and a Grerco V/P AGI variable speed counter agitating sweep mixer. The polyethylene, the mineral oil and the ethylene-vinyl acetate copolymer, together with other optional ingredients, including color, were combined at that stage.

The mixture was then heated to the recommended melting temperature of the highest melting point polymer and agitation commenced at about 20 rpm. When the mixture was completely melted and homogeneous, it was allowed to cool to 5° C. above the cloud point of the mixture in mineral oil. At this point, rapid cooling was accomplished by operating the mixer, at 35 rpm and by introducing 10° C. cooling water into the vessel jacket which rapidly cooled the mixture to a temperature 10° C. below the cloud point. A rate of cooling of approximately 1.5° C. per minute was maintained with continuous agitation.

The mixer was then operated at 20 rpm in order to minimize air entrapment into the composition and cooling was continued with agitation until the desired viscosity was attained. The mixture was then packaged. A gel formed after packaging as further cooling occurs with a maximum consistency being reached within 24 hours.

EXAMPLE 2

Following the procedure outlined in Example 1, a lip gloss composition was prepared utilizing the following formulation:

| | % by wt. |
|---|---|
| Light Mineral Oil (Visc. 100–125 cps.) | 42.83 |
| Polyethylene (M.W. 1000–1500) | 8.76 |
| Ethylene-Vinyl Acetate (M.W. 2000–2500) | 2.92 |
| Polybutene (Visc. 3000–3500 cps.) | 42.84 |
| Timiron Super Gold - colorant - titanated mica | 2.63 |
| D&C Red #6 barium lake; 15% colorant dispersion in lanolin oil | 0.02 |
| | 100.00 |

The viscosity of the lip gloss was determined after 24 hours at room temperature. The determination was made on a Brookfield Helipath RVT Spindle T-F at 10 rpm and 25° C. Recorded in 10,000 cps units, the first number is the reading on the downward path of the spindle and the second number is the upward path reading. The results obtained were 23/10. Similar determinations of the viscosity of the lip gloss at 4° C. and at 45° C. gave values of 80/76 and 16/12, respectively. After five months storage, at room temperature, the viscosity values at 25° C. varied by less than three units from the original determination.

EXAMPLE 3

The following composition was prepared into a lip gloss following the procedure set forth in Example 1:

| | % by wt. |
|---|---|
| Light Mineral Oil (Visc. 100–125 cps.) | 42.83 |
| Polyethylene (M.W. 1000–1500) | 2.92 |
| Ethylene-Vinyl Acetate (M.W. 2000–2500) | 8.76 |
| Polybutene (Visc. 3000–3500 cps.) | 42.84 |
| Timiron Super Gold | 2.63 |
| D&C Red #6 Lantrol Disp. 15% | 0.02 |
| | 100.00 |

The viscosity of the lip gloss was determined after 24 hours standing at room temperature. The determination was made on a Brookfield Helipath RVT Spindle T-F at 10 rpm and 25° C. Recorded in 10,000 cps units, the first number is the reading on the downward path of the spindle and the second number is the upward path reading. The results obtained were 27/20. At 45° C., the lip gloss showed a viscosity of 10/7, using the same procedure.

EXAMPLE 4

The following lip gloss composition was prepared following the procedure set forth in Example 1:

| | % by wt. |
|---|---|
| Light Mineral Oil (Visc. 100–125 cps.) | 42.83 |
| Polyethylene (M.W. 1000–1500) | 5.84 |
| Ethylene-Vinyl Acetate (M.W. 2000–2500) | 5.84 |
| Polybutene (Visc. 3000–3500 cps.) | 42.84 |
| Timiron Super Gold | 2.63 |
| D&C Red #6 Lantrol Disp. 15% | 0.02 |
| | 100.00 |

Viscosity of the lip gloss was determined after 24 hours using the procedure outlined in Example 3. The results obtained were less than 1 in both directions; the product was liquid.

EXAMPLE 5

Lip gloss compositions were prepared following the procedure set forth in Example 1, based on the following two formulations:

| | % by wt. | |
|---|---|---|
| | A | B |
| Light Mineral Oil (Visc. 100–125 cps) | 42.83 | 42.83 |
| Polyethylene (M.W. 1000–1500) | 11.68 | — |
| Ethylene-Vinyl Acetate (M.W. 2000–2500) | — | 11.68 |
| Polybutene (Visc. 3000–3500 cps.) | 42.84 | 42.84 |
| Timiron Super Gold | 2.63 | 2.63 |
| C&D Red #6 Lantrol Disp. 15% | 0.02 | 0.02 |
| | 100.00 | 100.00 |

Viscosity of each lip gloss was determined after 24 hours, using the procedure outlined in Example 3. Product A, with polyethylene only, had a viscosity of 40/21, and was too hard to readily expel from the container at room temperature. Product B, with the ethylene-vinyl copolymer only, had a viscosity of 1.5/<1 and was liquid at room temperature.

We claim:

1. A lip gloss comprising a mineral oil gel system comprising polyethylene having a molecular weight in the range of 1,000–25,000 and an ethylene-vinyl acetate copolymer having a molecular weight in the range of 2,000–3,000, wherein the weight proportion of the polyethylene to the ethylene-vinyl acetate copolymer is in the range of 90:10 to 70:30, respectively, where polyethylene is present in major proportion, and wherein the weight proportion of polyethylene to ethylene-vinyl acetate copolymer is in the range of 20:80 to 30:70, respectively, where the ethylene-vinyl acetate is present in major proportion, the lip gloss being a thermoplastic gel which maintains its consistency over the temperature range of 4° C. to 45° C., and having a viscosity in the range of 45,000 cps to 300,000 cps as determined on a Brookfield Helipath RVT Viscometer using a T-F spindle at 10 Rpm and at 25° C.

2. The lip gloss of claim 1, which additionally contains 43% by weight or less of a wear-enhancing agent selected from the group consisting of poly iso and normal butene, lanoline and dimethylpolysiloxane.

3. The lip gloss of claim 2, wherein the wear-enhancing agent is poly iso and normal butene.

4. The lip gloss of claim 1, wherein the weight proportion of polyethylene to ethylene-vinyl acetate copolymer is about 75:25, respectively, where the polyethylene is present in major proportion, and wherein the weight proportion of polyethylene to ethylene-vinyl acetate copolymer is about 25:75, respectively, where the ethylene-vinyl acetate copolymer is present in major proportion.

5. The lip gloss of claim 4, which additionally contains 43% by weight or less of poly iso and normal butene.

* * * * *